(12) United States Patent
Couture et al.

(10) Patent No.: US 9,545,375 B2
(45) Date of Patent: Jan. 17, 2017

(54) METHOD FOR ACTIVATING A CHEMICAL REACTION, SOLUTION THAT CAN BE ACTIVATED BY SAID METHOD AND DEVICE FOR IMPLEMENTING SAID METHOD

(71) Applicants: CENTRE NATIONAL DE LA RECHERCHE SCIENTIFIQUE - CNRS, Paris (FR); ECOLE SUPÉRIEURE DE PHYSIQUE ET CHIMIE INDUSTRIELLES DE LA VILLE DE PARIS, Paris (FR); INSERM - INSTITUT NATIONAL DE LA SANTÉ ET DE LA RECHERCHE MÉDICALE, Paris (FR)

(72) Inventors: Olivier Couture, Paris (FR); Mickael Tanter, Bagneux (FR); Patrick Tabeling, L'hay les Roses (FR); Janine Cossy, Paris (FR); Mathias Fink, Meudon (FR)

(73) Assignees: CENTRE NATIONAL DE LA RECHERCHE SCIENTIFIQUE—CNRS, Paris (FR); ECOLE SUPERIEURE DE PHYSIQUE ET CHIMIE INDUSTRIELLES DE LA VILLE DE PARIS, Paris (FR); INSERM (INSTITUT NATIONAL DE LA SANTE ET DE LA RECHERCHE MEDICALE), Paris (FR)

( * ) Notice: Subject to any disclaimer, the term of this patent is extended or adjusted under 35 U.S.C. 154(b) by 0 days.

(21) Appl. No.: 14/759,584

(22) PCT Filed: Jan. 3, 2014

(86) PCT No.: PCT/FR2014/050004
§ 371 (c)(1),
(2) Date: Jul. 7, 2015

(87) PCT Pub. No.: WO2014/108627
PCT Pub. Date: Jul. 17, 2014

(65) Prior Publication Data
US 2015/0343412 A1    Dec. 3, 2015

(30) Foreign Application Priority Data

Jan. 8, 2013 (FR) ...................... 13 50131

(51) Int. Cl.
| | | |
|---|---|---|
| A61K 9/00 | (2006.01) |
| A61K 41/00 | (2006.01) |
| B01J 19/10 | (2006.01) |
| B01F 13/00 | (2006.01) |
| B01F 15/02 | (2006.01) |

(52) U.S. Cl.
CPC ......... *A61K 9/0009* (2013.01); *A61K 41/0028* (2013.01); *B01F 13/0059* (2013.01); *B01F 13/0071* (2013.01); *B01F 15/0205* (2013.01); *B01J 19/10* (2013.01); *B01J 2219/00932* (2013.01); *B01J 2219/0875* (2013.01); *B01J 2219/0877* (2013.01)

(58) Field of Classification Search
CPC .................................. A61K 9/09; A61K 9/009
USPC ........................................................ 549/200
See application file for complete search history.

(56) References Cited

U.S. PATENT DOCUMENTS

| 6,244,738 B1 | 6/2001 | Yasuda et al. |
| 2011/0190627 A1 | 8/2011 | Tanter et al. |

FOREIGN PATENT DOCUMENTS

| GB | 2 453 534 A | 4/2009 |
| WO | WO 2010/026357 A1 | 3/2010 |
| WO | WO 2011/007082 A1 | 1/2011 |

OTHER PUBLICATIONS

International Search Report Application No. PCT/FR2014/050004 report dated Apr. 29, 2014.
Suslick KS, Crum LA "Sonochemistry and Sonoluminescence" in Encyclopedia of Acoustics 1997.
Culture O, Faivre M, Pannacci N, Babataheri A, Servois V, Tabeling P, Tanter M "Ultrasound Internal Tattooing" Medical Physics (2011) 38: 1116-1123.

*Primary Examiner* — Taofiq A Solola
(74) *Attorney, Agent, or Firm* — Miller, Matthias & Hull LLP

(57) ABSTRACT

The invention relates to a method which comprises emitting ultrasound into a liquid mixture containing first and second reagents in separate phases initially separated by a liquid precursor-gas barrier, the ultrasound having a high enough energy level to vaporize the precursor gas, such as to contact the reagents and thus to activate a chemical reaction therebetween.

12 Claims, 5 Drawing Sheets

METHOD FOR ACTIVATING A CHEMICAL REACTION, SOLUTION THAT CAN BE ACTIVATED BY SAID METHOD AND DEVICE FOR IMPLEMENTING SAID METHOD

CROSS-REFERENCE TO RELATED APPLICATION

This application is a 35 USC §371 U.S. National Stage filing of International Application No. PCT/FR2014/050004 filed on Jan. 3, 2014, and claims priority under the Paris Convention to French Patent Application No. 13 50131 filed on Jan. 8, 2013.

FIELD OF THE DISCLOSURE

The present invention relates to methods for activating chemical reactions, solutions that can be activated by such methods, and devices for implementing such methods.

BACKGROUND OF THE DISCLOSURE

Activation of chemical reactions between reagents is usually achieved by placing the reagents in contact with each other. However, the methods currently in use for achieving such contact do not always provide precise control, spatially and temporally, of the start of the chemical reaction between the reagents.

SUMMARY OF THE DISCLOSURE

The present invention is intended to solve this technical problem.

To this end, the invention provides a method for activating a chemical reaction in a solution forming a liquid mixture containing at least first and second reagents in distinct phases initially separated by at least one liquid gas-precursor barrier that can be vaporized by ultrasound, the method comprising an activation step wherein ultrasonic waves are emitted into the mixture, with an energy level sufficient to vaporize the gas precursor, thereby placing said reagents in contact with each other.

With these arrangements, upon activation of the emulsion by ultrasound, the vaporization of the gas precursor brings the reagents into intimate contact, which allows:
- obtaining a very rapid reaction between the reagents,
- very precisely controlling the moment the chemical reaction begins, with a precision that can be on the order of a microsecond for example,
- and/or forming, by the reaction between the reagents, a product which is quickly used at the site of its formation, which can be of particular interest when the product is unstable or difficult to transfer to the location where it will be used (for example, gaseous or non-soluble or non-encapsulatable product), or when it is particularly hazardous and could be harmful to the areas it traverses before reaching the target area.

The invention may also be of particular use for studying the kinetics of chemical reactions, due to the fact that the start time of the reaction is precisely controlled.

In various embodiments of the method according to the invention, one or more of the following arrangements may be applied:
- the ultrasound is emitted in a localized manner in a medium containing the mixture, so as to activate the reaction between the reagents only within a given target area;
- said reagents are initially contained in an emulsion comprising, in an outer solution, drops comprising at least the first reagent and said gas precursor, these being encapsulated by at least one emulsifier;
- the reagents are initially contained in a microtube and separated by at least one drop of gas precursor, and said at least one drop of gas precursor is vaporized during the activation step.

The invention also relates to a solution that can be activated by ultrasound, forming a liquid mixture containing at least first and second reagents in distinct phases separated by at least one liquid gas-precursor barrier that can be vaporized by ultrasound, said first and second reagents being intended to react with one another.

In various embodiments of the solution according to the invention, one or more of the following arrangements may possibly be used:
- the first and second reagents are contained in a microtube and are separated by at least one drop of gas precursor;
- the first and second reagents are contained in an emulsion comprising, in an outer solution, drops comprising at least the first reagent and said gas precursor, these being encapsulated by at least one emulsifier;
- said drops comprise a first outer emulsifier membrane and contain first primary drops containing the first reagent and second primary drops containing the second reagent, said first and second primary drops each being enclosed by a second emulsifier membrane and being in emulsion in the gas precursor;
- said drops are distributed into first and second groups of drops, the drops of the first group containing the first reagent and the drops of the second group containing the second reagent;
- said drops comprise a first outer emulsifier membrane and contain primary drops in emulsion in the gas precursor, said primary drops being enclosed by a second emulsifier membrane and containing either the first reagent or the second reagent;
- the second reagent is contained in the outer solution;
- said drops comprise a first outer emulsifier membrane and contain primary drops enclosed by a second emulsifier membrane, said primary drops being in emulsion in the gas precursor and the primary drops of at least some of said drops containing the first reagent;
- said gas precursor forms a barrier preventing diffusion of the first and second reagents;
- said drops have a diameter of less than 20 microns and said primary drops have a diameter of less than 5 microns;
- the gas precursor is a fluorinated oil;
- the gas precursor is a perfluorocarbon;
- the gas precursor is perfluorohexane and/or perfluoropentane;
- the outer membrane of the drops comprises a first emulsifier;
- the membrane of the primary drops contains a fluorinated surfactant;
- the fluorinated surfactant contains poly(perfluoropropylene glycol) carboxylate;
- the fluorinated surfactant is obtained from poly(perfluoropropylene glycol) carboxylate, perfluorocarbon, and ammonium hydroxide;
- the primary drops contain an inner liquid and the first reagent contained in the primary drops is in solution in the inner liquid.

Finally, the invention also relates to a device for implementing a method as described above, comprising:

at least one microtube comprising a solution that can be activated by ultrasound, forming a liquid mixture containing at least first and second reagents in distinct phases separated by at least one liquid gas-precursor barrier that can be vaporized by ultrasound, said first and second reagents being intended to react with each other, said liquid gas-precursor barrier comprising at least one drop of liquid gas-precursor, at least one acoustic transducer suitable for emitting ultrasound toward the drop of gas precursor in order to vaporize it and thereby cause said first and second reagents to react with each other.

BRIEF DESCRIPTION OF THE DRAWINGS

Other features and advantages of the invention will be apparent from the following description of three of its embodiments, given by way of non-limiting example, with reference to the accompanying drawings.

In the drawings.

DETAILED DESCRIPTION OF THE DISCLOSURE

In the various figures, the same references designate identical or similar elements.

The invention provides a method for activating by ultrasound a chemical reaction between at least first and second reagents A, B.

In general, the reagents A and B are initially contained in a solution forming a multiphase liquid mixture, where the reagents A, B are separated by a liquid gas-precursor which can be vaporized by ultrasound so as to activate a reaction between reagents A, B. Two embodiments of the invention, and a few variants, will now be described.

Figure 1:
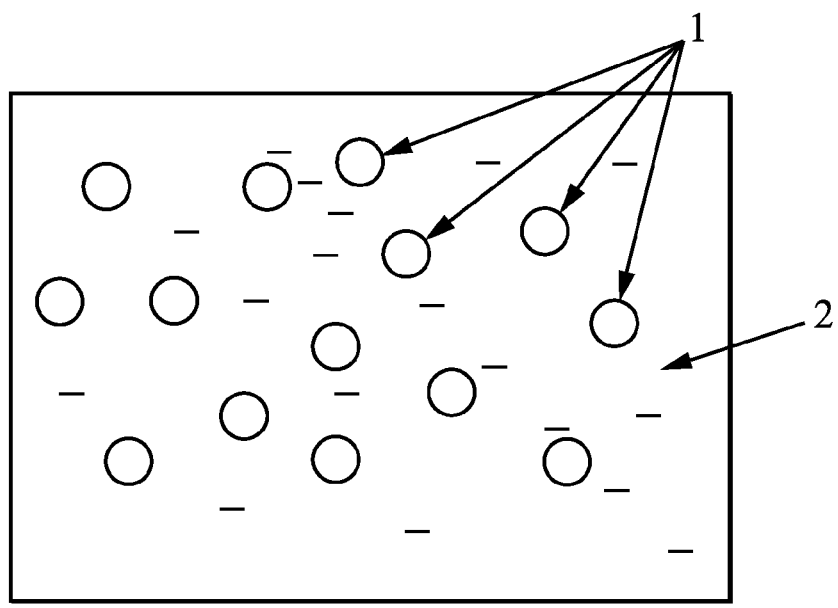
FIG. 1 is a schematic view of a solution containing microdrops in emulsion, usable in a first embodiment of the invention.
Figure 2:
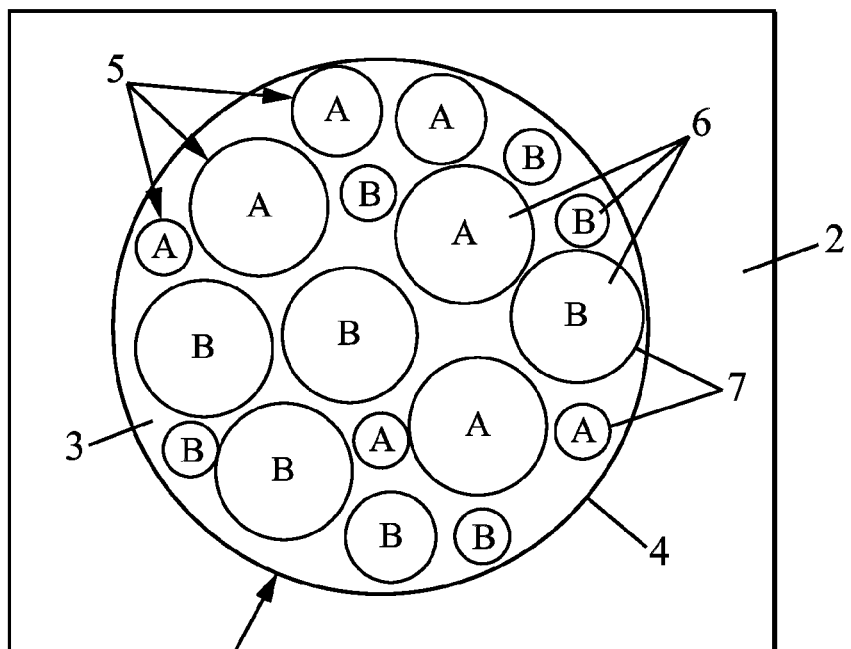
FIG. 2 is a schematic view of a microdrop of the emulsion of FIG. 1.

First Embodiment:

As shown schematically in FIGS. 1 and 2 for a first embodiment of the invention, the emulsion comprises microdrops 1 emulsified in a solution 2, for example an aqueous solution. These microdrops 1 may, for example, have a diameter D of less than 20 microns.

The diameter D is preferably less than 10 microns, for example smaller than 8 microns and in particular about 5 microns.

The microdrops 1 comprise a substantially spherical outer wall 4, formed by a first emulsifier, in particular a surfactant such as "Pluronic F68®" for example.

In the first embodiment represented in FIG. 2, there are two levels of emulsion with the microdrops 1 forming a secondary emulsion, and the outer wall 4 (liquid similar to the wall of a bubble) of each microbubble encapsulates a liquid gas-precursor 3 that can be vaporized by ultrasound, containing a primary emulsion of primary drops 5.

The gas precursor may be a fluorinated oil, in particular a perfluorocarbon, for example perfluorohexane or perfluoropentane.

The primary drops 5 have a diameter of less than 5 microns, preferably from 0.3 to 1 microns, for example about 500 nm. These primary drops 5 each have a substantially spherical outer wall 7 (liquid similar to the wall of a bubble) which is formed by a second emulsifier, for example a fluorinated surfactant such as poly(perfluoropropylene glycol) carboxylate (sold by DuPont under the trademark "Krytox 157 FSH®"). Specifically, the fluorinated surfactant may be prepared from poly(perfluoropropylene glycol) carboxylate, perfluorocarbon, and ammonium hydroxide. For example, this surfactant can be obtained by adding to 10 mg perfluorohexane, 10 mg Krytox 157 FSH® and 10 ml ammonium hydroxide (see Holze et al, "*Biocompatible surfactants for water-in-fluorocarbon emulsions*", *Lab Chip*, 2008, 1632-1639, *The Royal Society of Chemistry* 2008).

The outer wall 7 encapsulates an inner liquid 6, for example water or more generally an aqueous solution, containing an active agent. In the first embodiment of the invention, the primary drops are divided into two groups: a group of first primary drops where the active agent is a first reagent A, and a group of second primary drops where the active agent is a second reagent B. The first and reagents A, B are intended to react with each other to form a reaction product C, which may be an active agent, for example a drug or marker to be delivered to a precise location in the body of a patient. The active agent C may be, for example, a potent cytotoxic agent of short lifespan.

For example, the reagents A and B may be for example: A: 3-azido-7-hydroxycoumarin and B: 3-Hydroxy-2',3',2'', 3''-tetramethoxy-7,8-didehydro-1,2:5,6-dibenzo-cyclota-1, 5,6-triene, which react together to yield a fluorescent product.

Reagents A and/or B may be hydrophilic. Alternatively, they may possibly be hydrophobic, in which case they may be:

either in solution in a non-aqueous inner liquid 6, for example a fluorinated oil, or in emulsion in an aqueous inner liquid 6, the active agent then being encapsulated (for example with a fluorinated oil) in drops smaller than 1 micron (for example 0.3 to 0.4 microns) in emulsion in the inner liquid.

Given the fact that the primary drops are emulsified in the inner liquid 6, the first and second primary drops are intimately mixed.

In addition, the stability of the two levels of emulsion of the invention is particularly high because the gas precursor forms a barrier to diffusion of the reagents A and B and prevents them from reacting with one another prematurely, which extends the life of the product between manufacture and use, and eliminates an unintentional release of the reagents A, B and/or formation and diffusion of the reaction product C beyond the target area.

The two levels of emulsion described above can be obtained, for example, as described in document WO2011/007082A1.

When using the emulsion activatable by ultrasound, this emulsion may, for example, be released within a medium 29 (solid or not—for example part of a patient's body or some other medium), and the microdrops located within a target area 30 of the medium 29 can then be activated by using ultrasound to burst them.

Figure 3:
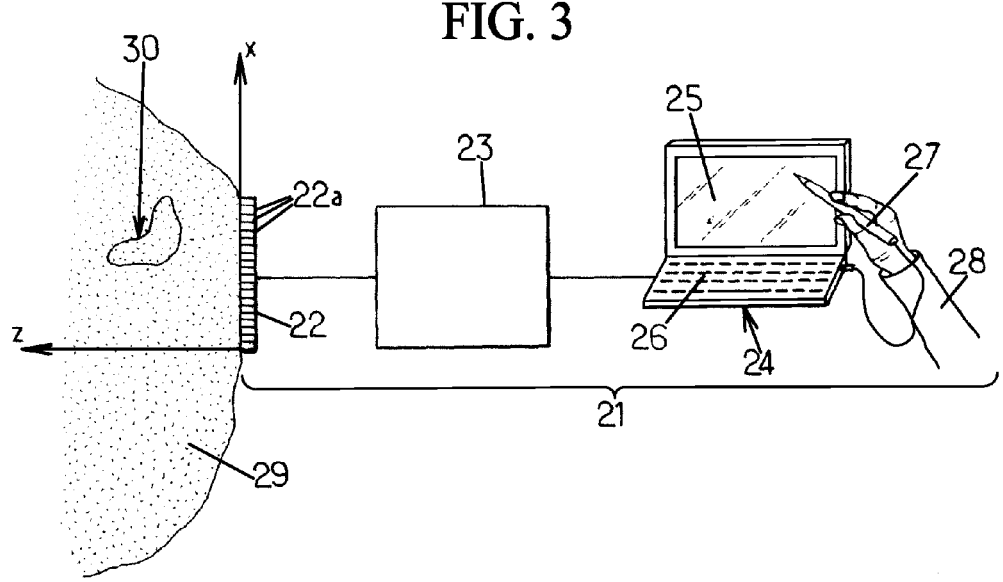
FIG. 3 is a general diagram showing an ultrasound device for locally activating an emulsion containing microdrops such as the one of FIG. 1.

In an exemplary embodiment, this may involve focused ultrasound which is emitted for example by an ultrasonic device 21 such as the one represented in FIG. 3. This is only an example, however, and the invention is not limited to this example.

This ultrasonic device 21 may be an ultrasonography imaging system comprising:
- an array 22 of ultrasonic transducers, for example a linear array of the type commonly used in ultrasonography, comprising a number n of ultrasonic transducers 22a (for example about 100 to 300 transducers, emitting for example at about 2.5 MHz), the transducer array 22 being intended for placement in contact with a medium 29,
- electronic controls 23 for controlling the pulses emitted from the transducer array 22 and for capturing signals read by the array,
- a computer 24 for controlling the electronic controls 23, the computer 24 having a user interface which includes a screen 25 on which ultrasound images captured by the transducer array 22 can be viewed, said user interface further comprising for example a keyboard 26 associated with a mouse or similar peripheral (not shown) and possibly a pointing device 27 such as a light pen or similar device, which for example allows an operator 28 to define an area on the screen 25 as will be explained below.

The electronic controls 23 and the computer 24 together form a control device for controlling the transducer array 22 and capturing and processing signals from the array. It is possible to have a single electronic device perform the functions of both the electronic controls 23 and the computer 24.

Figure 4:
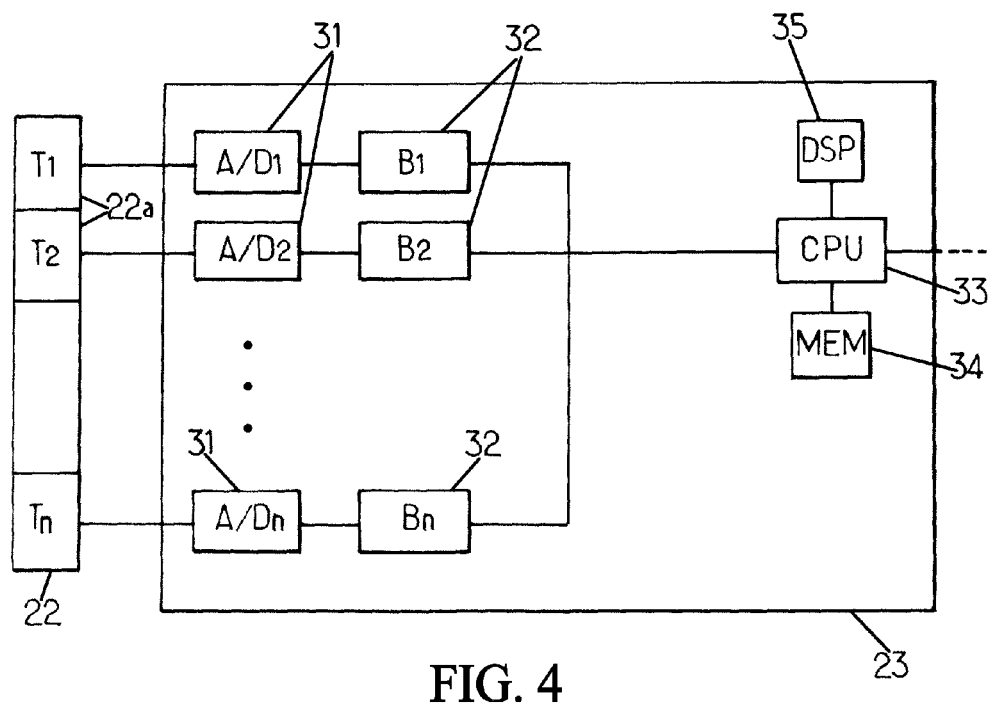
FIG. 4 is a block diagram of the device of FIG. 3, FIGS. 5 and 6 illustrate the ultrasonic activation of the emulsion of FIG. 2.

As represented in FIG. 4, the electronic controls 23 may comprise, for example:
- n analog-to-digital converters 31 ($A/D_1$-$A/D_n$) individually connected (for example by cable) to the n transducers ($T_1$-$T_n$) of the transducer array 22;
- n buffers 32 ($B_1$-$B_n$) respectively connected to the analog-to-digital converters 31,
- a central processing unit 33 (CPU) communicating with the buffers 32 and the computer 24,
- a main memory 34 (MEM) connected to the central processing unit 33,
- a signal processor 35 (DSP) connected to the central processing unit 33.

The device 21 may initially be used in conventional ultrasound imaging mode, for viewing an image of the target 30 on the screen 25. The operator 28 may, for example, define the target area 30 by drawing its outline on the screen 25, for example using said light pen 27 or any other user interface serving as a pointing device.

Figure 5:
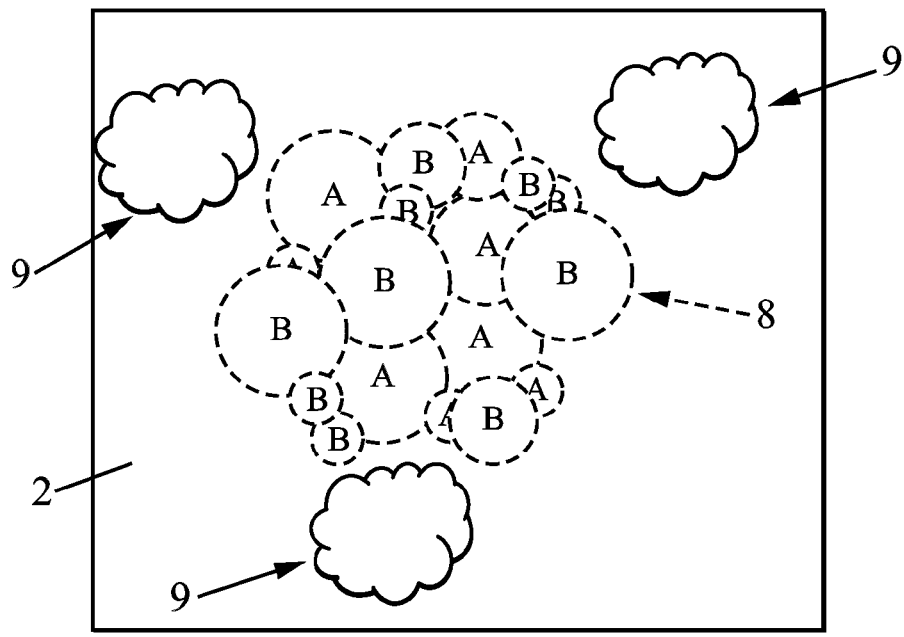

Once the target area 30 has been defined by the operator, he or she initiates the emulsion activation step by successively emitting activating ultrasonic beams focused at different points on said target area 30, such that the entire target area 30 is exposed to ultrasound which bursts the microdrops 1 it contains by vaporizing the gas precursor 3 of these microdrops, as symbolized by 9 in FIG. 5, leaving a remaining cluster 8 of primary drops 5 for a few nanoseconds or microseconds. Vaporization of perfluorocarbon occurs within a very short time, about the same as a period of the ultrasound which is on the order of a microsecond.

As the encapsulation of the primary drops 5 is no longer effective with a gas phase, and vaporization of perfluorocarbon is a violent phenomenon, the reagents A, B initially contained in the primary drops 5 are released nearly instantaneously.

Figure 6:
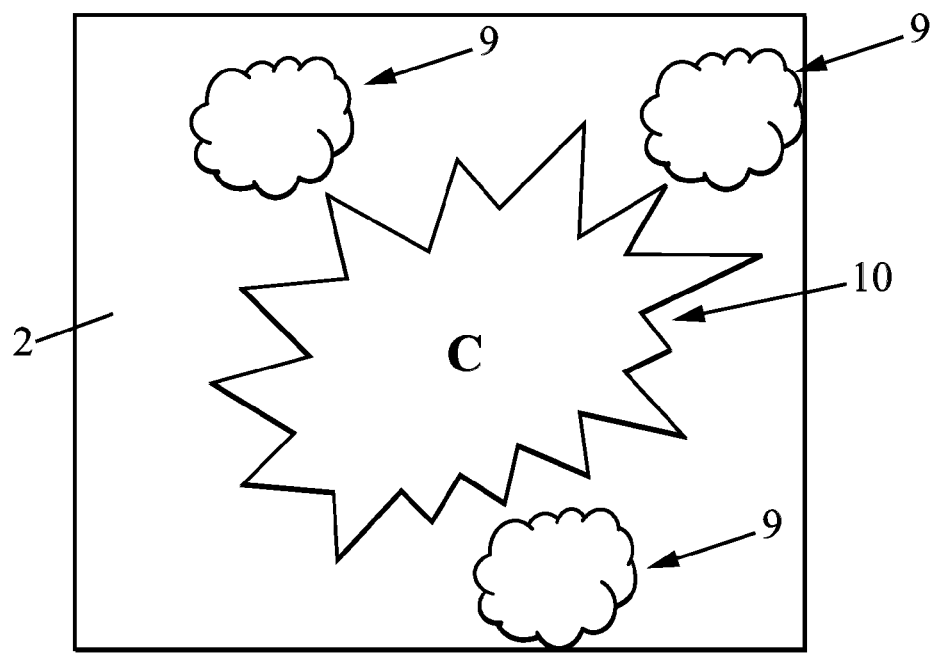

Following this nearly instantaneous release and due to the fact that the primary drops 5 containing the reagents A and B were initially intimately mixed and at most a few nanometers apart from each other, the reagents A and B immediately react to yield product C after about a microsecond (as symbolized by 10, FIG. 6).

This reaction time of about a microsecond is particularly fast in a chemistry context (for example, conventional methods for initiating rapid reactions such as stopped flow or microfluidic chips involve time scales beyond the millisecond).

Each activating ultrasound beam has a duration and power chosen to activate the emulsion as described above, without damaging the medium 29. For example, each activating ultrasound beam has a duration of 1 to 1000 microseconds, in particular from 10 to 1000 microseconds, and the power of said activating ultrasound beam is such that it exerts a pressure in the tissues of less than 8 MPa, in particular less than 6 MPa (megapascals), which corresponds to conventional imaging powers.

As already explained above, the invention thus enables delivery to the target area of active agents C that it was previously not possible to deliver, for example agents that are unstable or insoluble or gaseous or particularly hazardous or non-encapsulatable by emulsion, by transporting the reagents A and B in emulsion (A and B being stable and preferably soluble or at least encapsulatable by emulsion) and then forming these active agents C locally in the target area of use by ultrasonic activation of the emulsion.

In addition, focusing the ultrasound by controlling the phase of the transducers makes it possible to target the effect of the ultrasound to an area of a size which can be on the order of the wavelength (for example, about 300 microns at 5 MHz in water), which allows controlling the active agent C formation area with millimetric precision while not affecting areas where administration of the active agent C is unnecessary.

The invention is not limited to two-level emulsions of water-perfluorocarbon-water, but also applies to two-level emulsions of oil-perfluorocarbon-water or oil-perfluorocarbon-oil. The perfluorocarbon can also be replaced by another gas precursor that is ultrasound-activatable.

In addition, the emulsion according to the invention also allows initiating a reaction of more than two reagents, but more generally allows triggering by ultrasound at least one chemical reaction between n reagents A, B, D, . . . that are initially separated from each other by at least one emulsifier membrane, this reaction or reactions being triggered by destruction of said at least one emulsifier membrane by ultrasound.

Thus, in the case of at least three reagents A, B, D, . . . these reagents may initially be encapsulated separately in primary drops 5. In this case, one can either trigger an immediate reaction A+B+D->C, or when the reagents A, B, D are encapsulated in primary drops of different respective diameters, it is possible to release the various compounds A, B, D, . . . of the reaction sequentially, for example by sequentially applying different ultrasound pressures. It is thus possible to produce more complex reactions of the type A+B->X, X+D->C, and others.

Figure 7:
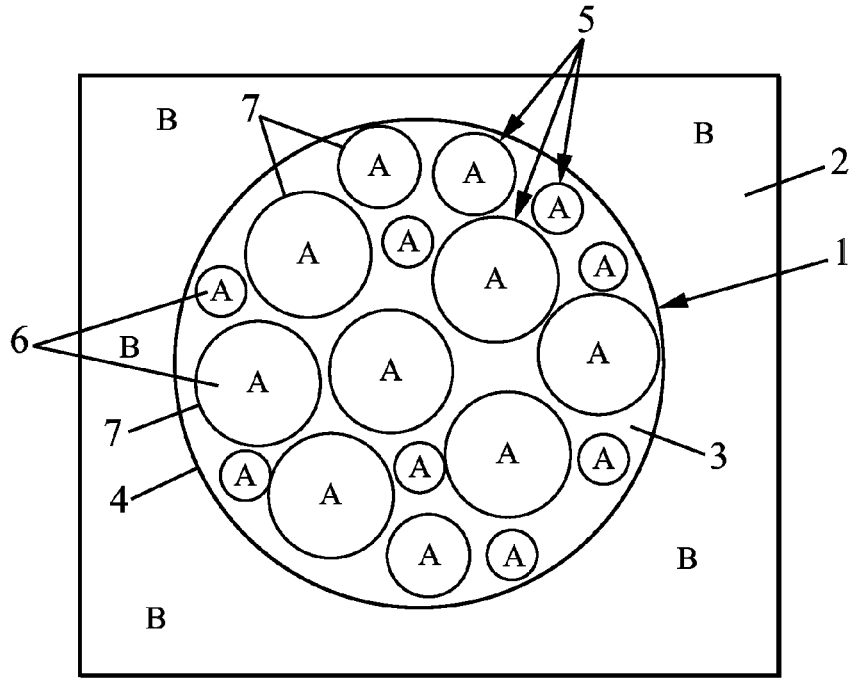
FIG. 7 is a schematic view of a microdrop of the emulsion of FIG. 1, according to a variant of the first embodiment of the invention.
Figure 8:
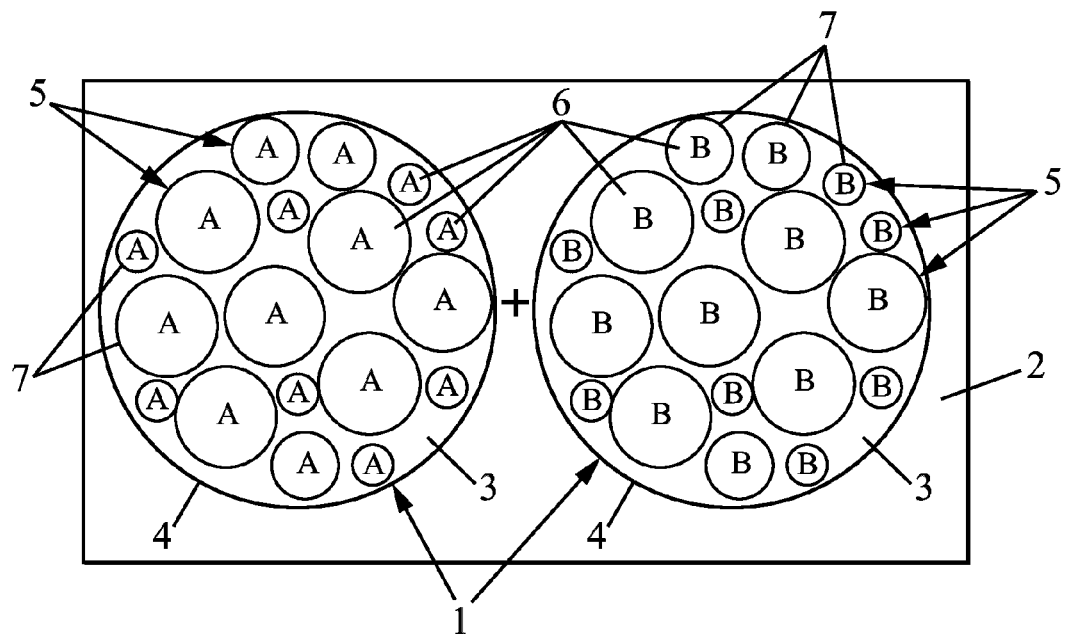
FIG. 8 is a schematic view of two microdrops of the emulsion of FIG. 1, according to another variant of the first embodiment of the invention.

Furthermore, the reagents A, B, D, . . . are not necessarily all contained in the same microdrops 1 of the emulsion:
- as represented in FIG. 7, one of the reagents may be in the solution 1 (reagent B in the example of FIG. 7, which is an example with two reagents);
- as represented in FIG. 8, the reagents may be in different microdrops 1.

The microdrops 1 of the embodiments of FIGS. 7 and 8 may have a two-level emulsion structure as described above and represented in the drawings, but they could possibly be simple emulsions (reagent A being directly in solution in the gas precursor in the case of FIG. 7, and reagents A, B being directly in solution in the gas precursor of their respective microdrops in the case of FIG. 8).

The invention can be implemented with any other type of device other than an imaging ultrasonograph, such as a single element transducer or one or more surface transducer(s).

Second Embodiment

Figure 9:
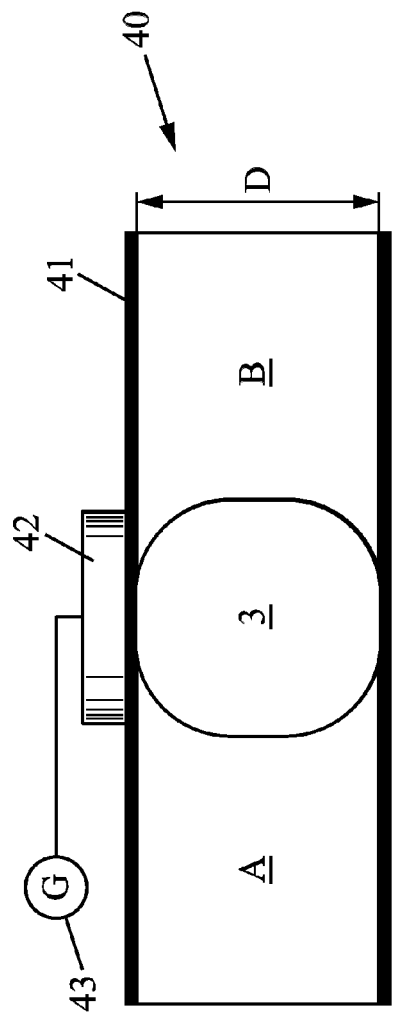
FIG. 9 shows an example of a microfluidic device containing a multiphase mixture usable in a second embodiment of the invention.

In the second embodiment of the invention represented in FIG. 9, the invention may be implemented in a microfluidic device 40 comprising at least a microtube 41, having a diameter or equivalent diameter D which may be about 5 to 20 microns for example and containing said first and second reagents A, B in the form of two distinct liquid phases separated by at least one drop of said liquid gas-precursor 3. The device 40 may further comprise at least one acoustic transducer 42 suitable for emitting ultrasound toward the drop of gas precursor 3 in order to vaporize it.

Figure 10:
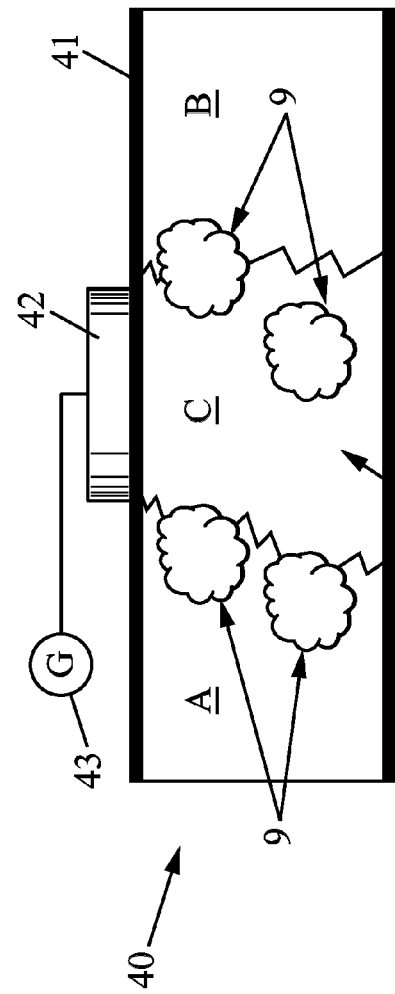
FIG. 10 is a view similar to FIG. 9, illustrating the ultrasonic activation of the multiphase mixture in the device of FIG. 9.

Once the drop of gas precursor has been vaporized by ultrasound emitted by the transducer 42 (FIG. 10), the reagents A and B react very rapidly as explained above for the first embodiment of the invention, to form the reaction product C.

The invention claimed is:

1. A method for activating a chemical reaction in a solution forming a liquid mixture containing at least first and second reagents in distinct phases initially separated by at least one liquid gas-precursor barrier that can be vaporized by ultrasound, said method comprising an activation step wherein ultrasonic waves are emitted into the mixture, with an energy level sufficient to vaporize the gas precursor, thereby placing said reagents in contact with each other.

2. The method according to claim 1, wherein the ultrasound is emitted in a localized manner in a medium containing the mixture, so as to activate the reaction between the reagents only within a given target area.

3. The method according to claim 1, wherein said reagents are initially contained in an emulsion comprising, in an outer solution, drops comprising at least the first reagent and said gas precursor, these being encapsulated by at least one emulsifier.

4. The method according to claim 1, wherein the reagents are initially contained in a microtube and separated by at least one drop of gas precursor, and said at least one drop of gas precursor is vaporized during the activation step.

5. A solution that can be activated by ultrasound, forming a liquid mixture containing at least first and second reagents in distinct phases separated by at least one liquid gas-precursor barrier that can be vaporized by ultrasound, said first and second reagents being adapted to react with one another.

6. The solution according to claim 5, wherein the first and second reagents are contained in a microtube and are separated by at least one drop of gas precursor.

7. The solution according to claim 5, wherein the first and second reagents are contained in an emulsion comprising, in an outer solution, drops comprising at least the first reagent and said gas precursor, these being encapsulated by at least one emulsifier.

8. The solution according to claim 7, wherein said drops comprise a first outer emulsifier membrane and contain first primary drops containing the first reagent and second primary drops containing the second reagent, said first and second primary drops each being enclosed by a second emulsifier membrane and being in emulsion in the gas precursor.

9. The solution according to claim 7, wherein said drops are distributed into first and second groups of drops, the drops of the first group containing the first reagent and the drops of the second group containing the second reagent.

10. The solution according to claim 9, wherein said drops comprise a first outer emulsifier membrane and contain primary drops in emulsion in the gas precursor, said primary drops being enclosed by a second emulsifier membrane and containing either the first reagent or the second reagent.

11. The solution according to claim 7, wherein the second reagent is contained in the outer solution.

12. A device for implementing a method according to claim 4, comprising:
- at least one microtube comprising a solution that can be activated by ultrasound, forming a liquid mixture containing at least first and second reagents in distinct phases separated by at least one liquid gas-precursor barrier that can be vaporized by ultrasound, said first and second reagents being adapted to react with each other, said liquid gas-precursor barrier comprising at least one drop of liquid gas-precursor,
- at least one acoustic transducer suitable for emitting ultrasound toward the drop of gas precursor in order to vaporize it and thereby cause said first and second reagents to react with each other.

* * * * *